United States Patent [19]

Carr et al.

[11] Patent Number: 5,474,762

[45] Date of Patent: Dec. 12, 1995

[54] SUNSCREEN AGENTS

[75] Inventors: Stuart W. Carr, Liverpool; Kevin R. Franklin, Heswall, both of United Kingdom; Charles C. Nunn, Bergen, N.J.; Jeffrey J. Pasternak, Morris, N.J.; Ian R. Scott, Allendale, N.J.

[73] Assignee: Chesebrough-Pond's USA Co. Division of Conopco, Inc., Greenwich, Conn.

[21] Appl. No.: 107,416

[22] Filed: Aug. 16, 1993

Related U.S. Application Data

[63] Continuation-in-part of Ser. No. 19,721, Feb. 19, 1993, abandoned.

[30] Foreign Application Priority Data

Feb. 21, 1992 [GB] United Kingdom .................. 9203806

[51] Int. Cl.$^6$ ................ A61K 7/40; A61K 7/42; A61K 7/44; C07F 7/28
[52] U.S. Cl. .............. 424/59; 423/179.5; 424/60; 556/49; 556/54; 556/55; 556/56
[58] Field of Search ................................. 424/59

[56] References Cited

U.S. PATENT DOCUMENTS

| | | | |
|---|---|---|---|
| 4,020,272 | 4/1977 | Tessler | 536/107 |
| 4,087,555 | 5/1978 | Barnett et al. | 252/316 |
| 4,129,645 | 12/1978 | Barnett et al. | 424/60 |
| 4,148,875 | 4/1979 | Barnett et al. | 424/80 |
| 4,664,843 | 5/1987 | Burba, III et al. | 252/315.5 |
| 4,790,954 | 12/1988 | Burba, III et al. | 252/315.5 |
| 5,015,409 | 5/1991 | Read, Jr. et al. | 252/108 |
| 5,073,573 | 12/1991 | Shanz et al. | 514/844 |
| 5,094,778 | 3/1992 | Burba, III et al. | 252/315.5 |
| 5,152,983 | 10/1992 | Nambudiry et al. | 424/59 |
| 5,154,932 | 10/1992 | Burba, III et al. | 424/605 |
| 5,196,143 | 3/1993 | Burba, III et al. | 252/309 |

FOREIGN PATENT DOCUMENTS

| | | | |
|---|---|---|---|
| 9-46344/89 | 6/1990 | Australia | 424/59 |
| 0207810 | 11/1988 | European Pat. Off. | C09K 7/02 |
| 0369275 | 11/1989 | European Pat. Off. | C01F 7/0002 |
| 0431755 | 6/1991 | European Pat. Off. | 424/59 |
| 2322584 | 4/1977 | France | 514/940 |
| 9119679 | 12/1991 | WIPO | C02F 1/56 |
| 9200355 | 1/1992 | WIPO | C09C 3/08 |

OTHER PUBLICATIONS

European Search Report in corresponding European Application No. 93301188.4.
Abstract of JP A 10 66 110—Patent Abstracts of Japan, vol. 13, No. 262, Jun. 16, 1989.
Copending application Serial No. 08/289,041, Aug. 11, 1994.
Copending application Serial No. 08/289,042, Aug. 11, 1994.
Derwent Abstract of JP 5001195, Jan. 8, 1993, Kaneka Corp.
Valim, Joao, et al. "Photoactivity of Cinnamate–intercalates of Layered Double Hydroxides". Mol. Cryst. Liq. Cryst. (1992), vol. 211, pp. 271–281.
Derwent Abstract of JP 3190811, Aug. 20, 1991, Shiseido.
Chibwe, Malama. "Synthesis, Characterization and Catalytic Properties of Mixed Metal Oxides". Nov. 1989, p. 95.
Meyn, Martina et al. "Anion–Exchange Reactions of Layered Double Hydroxides". Inorg. Chem. (1990). vol. 29, pp. 5201–5207.
Miyata, Shigeo. "Anion–Exchange Properties of Hydrotalcite–like Compounds". Clays and Clay Minerals, (1983) vol. 31, No. 4 pp. 305–311.

Primary Examiner—Dale R. Ore
Attorney, Agent, or Firm—Rimma Mitelman

[57] ABSTRACT

A sunscreen composition for application to human skin comprises an ultraviolet absorber which is introduced as an anion into a layered double hydroxide of the general formula

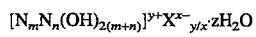

$$[M_m N_n(OH)_{2(m+n)}]^{y+} X^{x-}_{y/x} \cdot zH_2O$$

where M is a divalent metal or lithuin, N is a trivalent metal and X denotes anions present as an interlayer between layers of metal atoms joined through the OH groups.

Such layered double hydroxides are, for this invention, suspended in a cosmetically acceptable vehicle.

18 Claims, No Drawings

SUNSCREEN AGENTS

This is a continuation-in-part application of Ser. No. 08/019,721, filed Feb. 19, 1993, now abandoned.

This invention relates to sunscreen agents, that is to say compounds capable of absorbing ultra violet radiation with a wavelength in the range from 290 to 400 namometers. The invention also relates to sunscreen compositions for application to human skin incorporating the sunscreen agents.

In general terms, harmful ultra-violet (UV) rays, particularly those originating from sunlight, which penetrate the upper atmosphere and reach the earth's surface, can be classified into:

i. the energy-rich UV-B rays (290–320 nm wavelength) which possess an intense physiopathological activity on the skin; these are absorbed just above the dermis and they are responsible for erythema and skin pigmentation; and ii. UV-A rays (320–400 nm wavelength) which penetrate deeper into the skin (to the dermis and beyond). Their energy is much lower and the photobiological effects they cause are much more long term in nature, for example, they accelerate skin ageing.

Sunscreen compositions should desirably provide protection against both UV-A and UV-B rays, but protection against UV-A rays is particularly desirable, in order to prevent the long term photobiological effects resulting from UV-A radiation.

The naturally occurring mineral hydrotalcite is an example of a class of substances which are sometimes known as layered double hydroxides and have the general formula

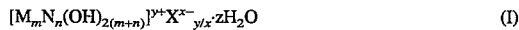

$$[M_mN_n(OH)_{2(m+n)}]^{y+}X^{x-}{}_{y/x} \cdot zH_2O \qquad (I)$$

In this formula N is one or more trivalent metal ions. M is one or more divalent metal ions or is lithium which is monovalent.

If M is divalent y=n, while if M is monovalent y=n-m. X is one or a mixture of anions.

In these substances the metal ions occur in layers in which the metal ions are connected together through the OH groups. The anions X are located in interlayers between the layers of metal ions. $x^-$ is the charge on the anion while $y^+$ is the charge on the mixed metal hydroxy cation.

The layered double hydroxides have been described in a number of documents including Meyn et al, Inorganic Chemistry, 29 5201 (1990) and Miyata, Clays and Clay Minerals, 31, 305 (1983). As referred to in those documents it is a characteristic of these double hydroxides that the anions X can undergo exchange with other anions. In natural hydrotalcite itself the interlayer anions are carbonate. In many of the double hydroxides which have been made synthetically the interlayer anions are inorganic although there have been some disclosures of incorporating organic anions including various aliphatic and aromatic carboxylates. Meyn et al, referred to above, disclose incorporating napthalene-1-sulphonate, salicylate and some other organics as an interlayer anion when the metals are zinc/aluminium, zinc/chromium or lithium/aluminium. Chibwa, PhD thesis University of Cambridge 1989, discloses incorporating chlorocinnamate as interlayer anion.

Various applications of layered double hydroxides have been referred to in the scientific literature, notably including use as chemical catalysts.

Broadly, the present invention provides layered double hydroxides in which at least some of the interlayer anions absorb ultra violet radiation in the range from 290 to 400 namometers, for application as sunscreen agents.

In a first aspect this invention provides a sunscreen composition for application to human skin comprising a cosmetically acceptable vehicle incorporating a layered double hydroxide of the formula

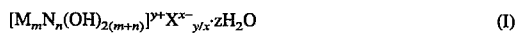

$$[M_mN_n(OH)_{2(m+n)}]^{y+}X^{x-}{}_{y/x} \cdot zH_2O \qquad (I)$$

wherein N is one or a mixture of trivalent metal ions, M is one or a mixture of divalent metal ions or is lithium, if M is divalent y=n and if M is lithium y=(n-m) and X denotes interlayer anions at least some of which display ultraviolet absorption over at least a portion of the wavelength range from 290 to 400 namometers.

In another aspect this invention provides use of layered double hydroxides in combination with defined above as sunscreen agents in. A third aspect of the invention is the layered double hydroxides as defined above, with the exception of the known materials in which a majority of the anions X are chlorocinnamate, salicylate or napthalene-1-sulphonate.

Certain preferred forms of this invention concern layered double hydroxides comprising interlayer anions which upon the incorporation into the layered double hydroxide display enhanced UV-A absorption compared to the UV-A absorption displayed by these anions prior to their incorporation.

In this invention the trivalent metal may be one or more of aluminium, chromium, iron, nickel, manganese, and scandium.

The divalent metal may be one or more of magnesium, zinc, calcium, cobalt, nickel, copper, manganese and iron.

As will be seen from these lists of possible ions, the transition metals nickel, manganese and iron may be in divalent or trivalent state. It is possible for at least some of these metals to provide both divalent and the trivalent ions in the same material.

In a layered double hydroxide, the ratio of monovalent or divalent ions to trivalent ions is defined by the ratio m/n. If a layered double hydroxide used in this invention has divalent metal ions M, then the ratio m/n preferably lies in the range 1 to 5. If it is monovalent ions M, then m/n is preferably in a range from 0.33 to 0.5.

The value of z will generally lie in a range from 0 to 10, more preferably 0 to 2, times the sum of m and n. This can be expressed as $$0 \leq \frac{z}{(m+n)} \leq 10$$

More preferably $$0 \leq \frac{z}{(m+n)} \leq 2$$

In general it will be desirable that the ultraviolet absorbing anions have a fairly strong absorption in at least a portion of the stated range from 290 to 400 namometers. This may be specified as a requirement that the acid form or a simple alkali metal or ammonium salt of the anion exhibits absorption with a molar extinction coefficient of at least $2 \times 10^3$, preferably $3 \times 10^3$, more preferably at least $5 \times 10^3$ and yet more preferably at least $8 \times 10^3$ over at least a portion of the stated wavelength range from 290 to 400 nm.

We have found that when such anions are incorporated as interlayer anions in a layered double hydroxide, their ultraviolet absorption is, in general, retained with little change.

In certain preferred embodiments of the invention, however, the anions employed are those anions which upon the incorporation into a layered double hydroxide display enhanced UV-A absorption compared to the UV-A absorption displayed by these anions prior to their incorporation. Thus, in preferred embodiments of the invention, enhanced UV-A protection is attained by virtue of incorporating specific anions (more fully described hereinafter) into a double layer hydroxide.

Effective ultraviolet absorption may be provided by an absorption band whose maximum is outside the stated range. For example the p-methoxy cinnamate ion has an absorption maximum at 285 namometers but the absorption band is broad enough to provide strong absorption over a range from 290 namometers up to at least around 320 namometers.

It will often be the case that absorption in the range 290 to 400 namometers will be provided by an absorption band with a maximum in the range 260 to 360 namometers.

Preferably the anions do not have strong absorption in the visible band from 400 to 700 namometers, especially in the part of it from 450 namometers upwards, notably from 450 or 500 to 650 namometers. The extinction coefficient for absorption in such ranges may preferably be no greater than $5 \times 10^2$ throughout the ranges concerned.

The molar extinction coefficient of a substance is usually measured in solution and is then given by the formula $$\epsilon = \frac{1}{cl} \log_{10} \frac{I_o}{I}$$

where I is the intensity of radiation transmitted through the sample, $I_o$ is the intensity of radiation transmitted through a reference sample consisting of the same solvent but without the substance under test, c is molar concentration in moles/liter, and 1 is the path length through the solution, in centimeters.

The proportion of interlayer anions X which absorb ultraviolet radiation may be fairly small, for example as little as 5 mole % of all the interlayer anions present, but may be higher such as a majority of the interlayer anions present and even up to 100%.

The interlayer anions which absorb ultraviolet radiation may be one or more of the following:

para amino benzimidazole-5-sulphonate 3-imidazol-4-yl acrylate salicylate p-methoxy cinnamate 2 ethyl hexyl-2-cyano-3,3 diphenyl acrylate 3,3,5 trimethylcyclohexyl-2-acetamido benzoate p-aminobenzoate cinnamate 3,4-dimethoxy phenyl glyoxylate α-(2-oxoborn-3-ylidene)-p-xylene-2-sulphonate α-(2-oxoborn-3-ylidene)toluene-4-sulphonate α-cyano-4-methoxy cinnamate 2-phenyl benzimidazole-5-sulphonate.

These anions, when in the free state, are known to display absorption in the wave length range from 290 to 400 namometers. All of them are regarded as acceptable materials to serve as sunscreen agents.

As mentioned above, we have now found that when they are incorporated as interlayer anions in a layered double hydroxide, their ability to absorb ultraviolet radiation is retained. In most instances, when the above-listed anions are incorporated into a layered double hydroxide, there is negligible change in the ultraviolet absorption spectrum.

Another group of organic materials suitable for the purposes of this invention are those which contain weak acid functionality through the inclusion of a phenolic proton or other weakly acidic proton in the molecule. It has been found, as part of the present invention, that this proton can be removed to form an anion which can be incorporated into a layered double hydroxide. The anions derived from such compounds may have absorption spectra significantly different from the parent compound, but nevertheless, these anions, upon incorporation into a layered double hydroxide, display significant absorption of light between 290 and 400 nm (UV-A region). In fact, in a preferred embodiment of this invention, advantage is taken of the fact that these materials display spectra when incorporated into layered double hydroxides so as to obtain enhanced UVA protection over that which would be obtained from the use of the parent compounds in the absence of the layered double hydroxide.

An important group of such phenolic compounds are hydroxylated benzophenone derivatives. Certain diketone compounds which can exist in a weakly acidic enol form may also be included. Examples of compounds from which anions employed in the preferred embodiment of the invention are derived include but are not limited to the following materials for which both CTFA and chemical names are given:

| CTFA Name | Chemical Name |
|---|---|
| Benzophenone-1 | 2,4-Dihydroxybenzophenone |
| Benzophenone-2 | 2,2',4,4'-Tetrahydroxybenzophenone |
| Benzophenone-3 | 2-Hydroxy-4-methoxy benzophenone |
| Benzophenone-4 | 2-Hydroxy-4-methoxy benzophenone-5-sulphonic acid |
| Benzophenone-5 | 2-Hydroxy-4-methoxy benzophenone-5-sulphonic acid; monosodium salt |
| Benzophenone-6 | 2,2'-Dihydroxy-4,4'-dimethoxy benzophenone |
| Benzophenone-7 | 5-Chloro-2hydroxy benzophenone |
| Benzophenone-8 | 2,2'-Dihydroxy-4-methoxy benzophenone |
| Benzophenone-9 | 2,2'-Dihydroxy-4,4'-dimethoxy benzophenone-3,3'-disulphonic acid; disodium salt |
| Benzophenone-10 | 2-Hydroxy-4-methoxy-4'-methyl benzophenone |
| Benzophenone-12 | 2-Hydroxy-4-octoxy benzophenone |
| Homosalate | Homomenthyl salicylate |
| Octyl Salicylate | 2-ethylhexyl salicylate |

Some tradenames and suppliers are:

| CTFA Name | Trade Name | Supplier |
|---|---|---|
| Benzophenone-1 | UVINUL 400 | BASF Chemical Co. |
| Benzophenone-2 | UVINUL D-50 | BASF Chemical Co. |
| Benzophenone-3 | UVINUL M-40 | BASF Chemical Co. |
| Benzophenone-4 | UVINUL MS-40 | BASF Chemical Co. |
| Benzophenone-5 | | Quest |
| Benzophenone-6 | UVINUL D-49 | BASF Chemical Co. |
| Benzophenone-7 | | Quest |
| Benzophenone-8 | SPECTRA-SORB UV-24 | American Cyanamide |
| Benzophenone-10 | UVISTAT 2211 | Ward Blenkinsop |
| Benzophenone-12 | CYASORB UV531 | American Cyanamide |
| Homosalate | KEMESTER HMS | Hunko Chemical |
| Octyl Salicylate | SUNARONE WMO | Felton Worldwide |

Another compound which can provide interlayer anions is Butyl Methoxydibenzoylmethane available as PARSOL 1789 from Givaudan Corp.

Also included in this form of the invention are anionic species derived from Pongomol which is a substituted 1,3-diketone whose systematic name is 1-(4-methoxy-5- benzofuranyl)-3-phenyl-1,3-propanedione. It has an ultraviolet absorption band within the range of from 250 to 500 nm, and an extinction coefficient of from 5,000 to 70,000. The diketone is more fully described in a commonly-assigned U.S. Pat. No. 5,152,983 incorporated by reference herein.

Among these materials, Benzophenone-4 and Benzophenone-9 have both a strong acid functionality conferred by a sulphonate group and weak acid functionality, conferred by the phenolic proton. For these materials (and for Benzophenone-5 which is the monosodium salt of Benzophenone-4), multiple anionic forms of the material may be produced and incorporated into layered double hydroxides. Thus, for example, with Benzophenone-4, both an mono- and dianion can be incorporated into layered double hydroxides. Both monoanionic and dianionic forms of this material and any combinations thereof incorporated into layered double hydroxides may be useful for sunscreens and are to be considered within the scope of this invention.

Layered double hydroxides are insoluble both in water and in other solvents. They can however be suspended as dispersions in solvents including water. A sunscreen composition according to this invention will therefore have the layered double hydroxide, with ultraviolet-absorbing. interlayer anions, dispersed in the vehicle. Preferably the vehicle is aqueous and the layered double hydroxide is suspended in this. For use the composition is rubbed onto skin and the water then evaporates, along with any volatile organic compounds included in the vehicle. This leaves the layered double hydroxide along with the ultraviolet absorbing anions as a deposit on the skin. The layer structure of the material assists in the deposition of the ultraviolet absorbing material as a continuous layer on the skin.

The aqueous vehicle may be an oil-in-water emulsion with the layered double hydroxide suspended in that emulsion. Many of the layered double hydroxides will suspend in the aqueous phase of such an emulsion but some are hydrophobic and suspend in the oil phase.

Layered double hydroxides are insoluble materials and are macromolecules so that the molecular size is .large compared with the size of the organic compounds which are conventional sunscreen agents.

These properties are advantageous. Once layered double hydroxides have been deposited on the skin, their large molecular size and/or their insolubility means that they should not be prone to penetrating into the skin, nor to moving about on the skin surface. (Penetration into the body through the skin and migration to sensitive areas such as the eyes are both potential hazards with water-soluble sunscreen active agents). Because the materials of the invention are insoluble, they also cannot dissolve away while the user is swimming, which provides a further advantage.

We have found that the ultraviolet absorbing organic interlayer anions are not prone to ion exchange with chloride ion in aqueous solution, indicating that these anions will not be leached out by ion exchange on contact with sea water.

A sunscreen composition containing a layered double hydroxide in accordance with this invention can be prepared by adding the layered double hydroxide to an aqueous vehicle, which at its simplest may be water alone, and then mixing to form a suspension. The layered double hydroxides are self-thickening and self-suspending, that is to say when they are dispersed in water the presence of the dispersed layered double hydroxide enhances the viscosity and automatically assists in maintaining the solid in suspension.

It is envisaged that a sunscreen composition according to this invention will contain from 0.05 to 50% by weight of the layered double hydroxide, more preferably from 0.1 to 30% by weight, yet more preferably 2 to 20% by weight. The amount which is incorporated will affect the amount of ultraviolet absorption achieved, of course. Therefore amounts towards the upper end of the range would be used for sunscreen compositions intended to give a high degree of protection against ultraviolet radiation.

Other materials may be included in sunscreen compositions according to this invention. It is within the scope of this invention to incorporate an additional sunscreen agent. Possibilities include nonionic organic sunscreen agents, inorganic sunscreen agents such as finely divided titanium dioxide and particles of organic polymers.

Other materials which may possibly be included in a sunscreen composition include emollient oils, humectants and fluids to enhance lubricity, notably silicone oils. Minor constituents which may be present include perfume and preservatives.

Preparation of a layered double hydroxide incorporating ultraviolet absorbing interlayer anions will generally take place in two stages: the first stage being the preparation of a layered double hydroxide with some other anions and the second stage being ion exchange to replace at least some of the anions with ultraviolet absorbing anions.

There are numerous techniques disclosed in the literature for the preparation of layered double hydroxides. We have found it satisfactory to treat suspension of an oxide of one metal with a soluble salt, notably a nitrate, chloride or sulphate of another metal, preferably at an elevated temperature, followed by filtering off the solid.

The layered double hydroxides can be identified by chemical analysis for the elements present and by X-ray diffraction.

Ion exchange to introduce the ultraviolet absorbing interlayer anions can be carried out by suspending a layered double hydroxide in an aqueous solution of the anions which it is desired to introduce. The process may be carried out at an elevated temperature to increase the speed of reaction. The layered double hydroxide may then filtered off or the suspension so formed of layered double hydroxide containing UV absorbing anion may be utilized directly to prepare a sunscreen (See Examples 24 and 25). It can be characterised by chemical analysis and by ultraviolet spectroscopy carried out on an aqueous suspension of the layered double hydroxide.

Different anions have different affinities for the interlayer sites in layered double hydroxides. We have found that organic anions are, generally, able to displace sulphate, chloride and nitrate anions, enabling them to be incorporated into layered double hydroxides by ion exchange.

The carbonate form of layered double hydroxides can be used as a starting material if the desired ultra-violet absorbing species is used in its acid (hydrogen ion) form rather than as a salt. In this case the carbonate anion is displaced by a decomposition reaction rather than by ion exchange.

EXAMPLES

Example 1

Preparation of Magnesium Aluminium Hydroxy Nitrate 46.8 g of magnesium oxide was suspended in 250 ml of distilled water in a one liter polypropylene screwcap bottle. 145.1 g of hydrated aluminium nitrate ($Al(NO_3)_3 \cdot 9H_2O$) were dissolved in 500 ml of distilled water and the resulting solution was added, with stirring, to the magnesium oxide suspension. The bottle was capped, shaken vigorously for 2 minutes and then placed in a thermostated oven for 5 days at 90° C. At the end of this period the solid was filtered off, washed thoroughly with water and then freeze dried. The dried material was finally equilibrated with water vapour by storing in a desiccator over a saturated sodium chloride solution.

The chemical composition of this material was determined by analysis. The results were as follows:

| Mole ratio Mg/Al | = | 2.0 |
|---|---|---|
| % MgO + Al$_2$O$_3$ | = | 49.8 |
| % H$_2$O (from dehydroxylation) | = | 16.7 |
| % NO$_3$ | = | 23.2 |

This is consistent with a formula for the anhydrous material of Mg$_4$ Al$_2$ (OH)$_{12}$ (NO$_3$)$_2$ The X-ray diffraction pattern of the hydrated material showed
i) the only crystalline material present was a layered double hydroxide analogous to hydrotalcite. Characteristic line spacings at 1.48A and 1.51A were present.
ii) there was a major line at 8.8A, which has been shown to be characteristic of this interlayer nitrate containing material.

The uv spectrum of a suspension of $2\times10^{-2}$ g/kg of the material in water, measured over the range 250 to 500 nm (which of course extends somewhat into the visible range) showed no absorption bands.

Example 2

Ion-exchange of Cinnamate Anion into Magnesium Aluminium Hydroxy Nitrate 13.47 g of cinnamic acid were dissolved/suspended in 150 ml of water. 5.1 g of potassium hydroxide were dissolved in 50 ml of water, and then this was added to the suspension to give a clear solution. This solution was added to 25 g of the nitrate form of layered double hydroxide as made in Example 1 in a 250 ml polypropylene screwcap bottle. The bottle was capped, shaken for 2 minutes, and then heated at 90° C. for 2 hours. The solid was filtered off, washed with warm water and then freeze dried. The produce was finally equilibrated with water vapour by storing in a desiccator over a saturated sodium chloride solution.

The chemical composition of the material obtained was determined by analysis. The results were as follows:

| % MgO + Al$_2$O$_3$ | = | 40.4 |
|---|---|---|
| % C | = | 23.0 |

This is consistent with a formula for the anhydrous material of

Mg$_4$Al$_2$(OH)$_{12}$(cin)$_{1.4}$(NO$_3$)$_{0.6}$ where cin=cinnamate.
The X-ray diffraction pattern showed
i) the only crystalline material present was a layered double hydroxide.
ii) there was a major line at 16.9A, which was not present in the starting material.

The uv spectrum of a suspension of $1.6\times10^{-2}$ g/kg of the material in water, measured over the range 250 to 500 nm showed a single peak centred at 268 nm. Solutions of sodium cinnamate and cinnamic acid also show a single peak close to this wavelength.

Example 3

The procedure of Example 2 was repeated, but modified in that the amount of cinnamic acid and potassium hydroxide were doubled (26.94 g cinnamic acid and 10.2 g potassium hydroxide) and the reaction time increased to 18 hours.

The chemical composition of the material was determined by analysis. The results were as follows:

| % MgO + Al$_2$O$_3$ | = | 36.29 |
|---|---|---|
| % C | = | 27.34 |

This is consistent with a formula for the anhydrous material of

Mg$_4$Al$_2$(OH)$_{12}$(cin)$_{1.84}$(NO$_3$)$_{0.16}$ where cin=cinnamate.
This example thus demonstrates that an increased amount of cinnamate can be introduced by ion exchange.

Example 4

Ion-exchange of p-Methoxy Cinnamate into Magnesium Aluminium Hydroxy Nitrate

The procedure of Example 3 was modified in that the cinnamic acid was replaced by 32.36 g p-methoxy cinnamic acid.

The chemical composition of the material obtained was determined by analysis. The results were as follows:

| % MgO + Al$_2$O$_3$ | = | 33.51 |
|---|---|---|
| % C | = | 29.05 |

This is consistent with a formula for the anhydrous material of

Mg$_4$Al$_2$(OH)$_{12}$(mcin)$_{1.90}$(NO$_3$)$_{0.10}$ where mcin=p-methoxy cinnamate.
The x-ray diffraction pattern showed
i) the only crystalline material present was layered double hydroxide.
ii) there was a major line at 18.2A which was not present in the starting material.

The uv spectrum of a suspension of $2.5\times10^{-2}$ g/kg of the material in water, measured over the range 250 to 500 nm showed a broad peak centred at 285 nm.

Example 5

Ion-exchange of 2-Phenylbenzimidazole-5-sulphonate into Magnesium Aluminium Hydroxy Nitrate The procedure of Example 2 was modified in that the cinnamic acid was replaced with 24.9 g of 2-phenylbenzimidazole-5-sulphonic acid, and the potassium hydroxide replaced with 3.6 g sodium hydroxide.

The chemical composition of the material obtained was determined by analysis. The results were as follows:

| | | |
|---|---|---|
| % MgO + Al$_2$O$_3$ | = | 35.47 |
| % C | = | 23.98 |

This is consistent with a formula for the anhydrous material of $$Mg_4Al_2(OH)_{12}(pbs)_{1.14}(NO_3)_{0.86}$$

where pbs=2-phenylbenzimidazole-5-sulphonate.

The X-ray diffraction pattern showed i) the only crystalline material present was layered double hydroxide.

ii) there was a major line at 22A, which was not present in the starting material.

The uv spectrum of a suspension of $2.5 \times 10^{-2}$ g/kg of the material in water, measured over the range 250 to 500 nm showed a broad peak with a maximum at 304 nm. Solutions of sodium 2-phenylbenzimidazole-5-sulphonate and 2-phenylbenzimidazole-5-sulphonic acid also show a similar peak.

Example 6

The procedure of Example 5 was varied by increasing the reaction time from 2 hours to 18 hours.

The chemical composition of the material obtained was determined by analysis. The results were as follows:

| | | |
|---|---|---|
| % MgO + Al$_2$O$_3$ | = | 27.92 |
| % C | = | 28.08 |

This is consistent with a formula for the anhydrous material of $$Mg_4Al_2(OH)_{12}(pbs)_{1.70}(NO_3)_{0.30}$$

where pbs=2-phenylbenzimidazole-5-sulphonate.

Example 7

The procedure of the Example 6 was varied by doubling the amounts of 2-phenylbenzimidazole-5-sulphonic acid and sodium hydroxide.

The chemical composition of the material obtained was determined by analysis. The results were as follows:

| | | |
|---|---|---|
| % MgO + Al$_2$O$_3$ | = | 27.63 |
| % C | = | 29.21 |

This is consistent with a formula for the anhydrous material of $$Mg_4Al_2(OH)_{12}(pbs)_{1.78}(NO_3)_{0.22}$$

where pbs=2-phenylbenzimidazole-5-sulphonate.

Example 8

Ion-exchange of Benzophenone-4 into Magnesium Aluminium Hydroxy Nitrate 7.41 g of 2-hydroxy-4-methoxy benzophenone-5-sulphonic acid (Benzophenone-4) were dissolved in 150 ml of water. 1,35 g of potassium hydroxide were dissolved in 50 ml of water, and then the two solutions were combined. This solution was added to 6.25 g of the magnesium aluminium hydroxy nitrate formed in Example 1 in a 250 ml polypropylene screwcap bottle. The bottle was capped, shaken for two minutes, and then heated at 90° C. for 2 hours. The solid was filtered off, and contacted with a fresh, identical solution of 2-hydroxy-4-methoxy benzophenone-5-sulphonic acid and potassium hydroxide. The mixture was heated at 90° C. for 18 hours. The solid material was then filtered off, washed with warm water, and freeze dried. The material was finally equilibrated with water vapour by storing in a desiccator over saturated sodium chloride solution.

The chemical composition of the material obtained was determined by analysis. The results were

| | | |
|---|---|---|
| % MgO + Al$_2$O$_3$ | = | 34.57 |
| % C | = | 25.42 |

Infra Red spectroscopy showed no evidence of residual nitrate in the material. This is consistent with a formula for the anhydrous material of $$Mg_4Al_2(OH)_{12}(Benz)_{1.16}$$

where Benz is the anion of 2-hydroxy-4-methoxy benzophenone-5-sulphonic acid, i.e. the anion of Benzophenone-4.

The Benzophenone-4 anion appears to be located in the structure partially as a monovalent species and partially as a divalent species.

The x-ray diffraction pattern showed i) the only crystalline material present was layered double hydroxide.

ii) there were major lines at 20A and 13.4A which were not present in the starting material. (The 20A line corresponds to layers which contain predominantly the monovalent species and the 13.4A line to layers with the divalent species.

The uv spectrum of a suspension of $5 \times 10^{-2}$ g/kg of the material in water, measured over the range 250 to 500 nm, contains a broad absorption band with peaks centred at about 250, 285, 320 and 365 mm.

Example 9

Ion-exchange of Benzophenone-4 into Magnesium Aluminium Hydroxy Nitrate 28 g of Benzophenone-4 and 7.2 g of sodium hydroxide were dissolved in 200 ml of distilled water to produce a bright yellow solution. This was added to 25 g of the nitrate form of layered double hydroxide, as made in Example 1, in a 250 ml polypropylene screwcap bottle. The bottle was capped, shaken for 2 minutes, and then heated at 90° C. for 2 hours. The solid was filtered off, washed with warm water and then freeze dried. The product was finally equilibrated with water vapour by storing in a desiccator over a saturated sodium chloride solution for 24 hours.

The chemical composition of the material obtained was determined by chemical analysis. The results were

| | | |
|---|---|---|
| % MgO + Al$_2$O$_3$ | = | 40.47 |
| % C | = | 20.90 |

| | | |
|---|---|---|
| % N | = | 0.82 |

This is consistent with a formula for the anhydrous material of $Mg_4 Al_2 (OH)_{12} (Benz)_{0.81} (NO_3)_{0.38}$ where Benz is an anion of Benzophenone-4 The x-ray diffraction pattern showed i) that the only crystalline material present was a layered double hydroxide.

ii) there was a major line at 13.3A which was not present in the starting material. (This corresponds to layers which contain predominantly divalent anions of benzophenone-4.

The uv spectrum of a suspension of $4 \times 10^{-2}$ g/kg of the material in water, measured over the range 250 to 500 nm, contains a broad absorption band with peaks centred at about 250, 285 and 365 nm.

Example 10

Ion-exchange of Benzophenone-4 into Magnesium Aluminium Hydroxy Chloride

A sample of a magnesium aluminium hydroxy chloride (Drilling Fluid Additive XUS 50165.04L) was obtained from the Dow Chemical Company. The material is of the type described in patent EP-A-207810 and corresponding U.S. Pat. Nos. 4664843, 4790954 and 5094778. X-ray diffraction analysis of this material showed the major crystalline phase to be a layered double hydroxide with a basal spacing of 7.8A.

4.95 g of Benzophenone-4 and 1.29 g of sodium hydroxide were dissolved in 40 ml of distilled water to produce a bright yellow solution. This was added to 10 g of the DOW material described above in a 250ml polypropylene screwcap bottle. The bottle was capped, shaken for 2 minutes, and then heated at 90° C. for 2 hours. The solid was filtered off, washed with warm water and then freeze dried. The product was finally equilibrated with water vapour by storing in a desiccator over a saturated sodium chloride solution for 24 hours.

The chemical composition of the material obtained was determined by chemical analysis. The results were

| | | |
|---|---|---|
| % MgO + Al$_2$O$_3$ | = | 46.63 |
| % C | = | 18.01 |

This is consistent with a formula for the anhydrous material of $Mg_4Al_4(OH)_{16}(Benz)_{0.8}(Cl,OH)_{0.4}$ The x-ray diffraction pattern showed i) that the major crystalline phase present was a layered double hydroxide.

ii) there was a major line at 13.8A which was not present in the starting material.

Example 11

Ion-exchange of Benzophenone-3 into Magnesium Aluminium Hydroxy Nitrate

Into 350 ml of deionized water was dissolved 4.5 g of NaOH and 17.1 g of Benzophenone-3. This solution was then added to a bottle containing 14.1 g of magnesium aluminium hydroxy nitrate prepared essentially as described in Example 1. The mixture was shaken and allowed to stand at room temperature for 18 hours. The yellow solid which was obtained was then washed in a medium porosity fritted funnel with 1500 ml of ethanol followed by 1000 ml of water at 80° C. The resulting solid was filtered and freezed dried to obtain a dry free-flowing yellow powdered solid.

The chemical composition of this material was determined by analysis. The results were as follows:

| | | |
|---|---|---|
| % MgO + Al$_2$O$_3$ | = | 54.5 |
| % C | = | 5.25 |

This is consistent for a formula for the anhydrous material of $Mg_4AL_2(OH)_{12}(Bz3)_{0.15}(NO_3)_{0.49}(OH)_{1.36}$ where Bz3 is the anion derived from Benzophenone-3.

The x-ray diffraction data showed that:

i) the only crystalline material present was layered double hydroxide.

ii) there was a major line at 11.8A which was not present in the starting material.

Example 12

Ion-exchange of Benzophenone-3 into Magnesium Aluminium Hydroxy Nitrate 8.6 g of Benzophenone-3 was dissolved in 50 ml ethanol and added to a 1.5 g of sodium hydroxide in 50 ml of distilled water to give a yellow solution. This was added to 10 g of the nitrate form of layered double hydroxide, made as in-Example 1, in a 250 ml polypropylene screwcap bottle. The bottle was capped, shaken for 2 minutes, heated at 90° C. for 20 minutes and then stirred gently for 3 hours at room temperature. The solid was filtered off and then repeatedly washed with portions of ethanol and then hot water. The solid product was freeze dried and equilibrated with water vapour.

The chemical composition of the material obtained was determined by chemical analysis. The results were

| | | |
|---|---|---|
| % MgO + Al$_2$O$_3$ | = | 47.47 |
| % C | = | 12.45 |
| % N | = | 1.35 |

This is consistent with a formula for the anhydrous material of $Mg_4AL_2(OH)_{12}(Bz3)_{0.41}(NO_3)_{0.53}(OH)_{1.06}$ where Bz3 is the anion derived from Benzophenone-3.

The x-ray diffraction pattern showed i) that the only crystalline material present was a layered double hydroxide.

ii) there was a major line present at 11.5A which was not present in the starting material and which is characteristic of a benzophenone-3 exchanged material.

Example 13

Ion-exchange of Benzophenone-8 into Magnesium Aluminium Hydroxy Nitrate 9.2 g of Benzophenone-8 was dissolved in 50 ml ethanol and added to 1.5 g of sodium hydroxide in 50 ml of distilled water to give a deep orange solution. This was added to 10 g of the nitrate form of layered double hydroxide, made as in Example 1, in a 250 ml polypropylene screwcap bottle. The bottle was capped, shaken for 2 minutes, heated at 90° C. for 1 hour and then stirred gently for 2 hours at room temperature. The solid was filtered off and then repeatedly washed with portions of thanol and then hot water. The solid product was freeze dried and equilibrated with water vapour.

The chemical composition of the material obtained was determined by chemical analysis. The results were

| % MgO + $Al_2O_3$ | = | 48.67 |
| % C | = | 9.42 |
| % N | = | 1.64 |

This is consistent with a formula for the anhydrous material of $Mg_4Al_2(OH)_{12}(Bz8)_{0.3}(NO_3)_{0.63}(OH)_{1.07}$ where Bz8 is the anion derived from Benzophenone-8. The x-ray diffraction pattern showed
 i) that the only crystalline material present was a layered double hydroxide.
 ii) there was a major line present at 17.0A which was not present in the starting material and which is characteristic of a benzophenone-8 exchanged material.

Example 14

Ion-exchange of Butyl Methoxydibenzoylmethane (Parsol 1789) into Magnesium Aluminium Hydroxy Nitrate 11.62 g of Parsol 1789 was suspended in 100 mo of a 1:1 by weight distilled water - ethanol mixture, and added to 1.5 g of sodium hydroxide in 50 ml of distilled water to give a bright yellow solution/suspension. This was added to 10 g of the nitrate from layered double hydroxide from Example 1 in a 250 ml polypropylene screwcap bottle. The bottle was capped, shaken for 2 minutes and heated at 90° C. for 6 hours. The solid was filtered off and then repeatedly washed with portions of acetone and then hot water. The solid product was freeze dried and equilibrated with water vapour.

The chemical composition of the material obtained was determined by chemical analysis. The results were

| % MgO + $Al_2O_3$ | = | 37.58 |
| % C | = | 27.68 |
| % N | = | 0.72 |

This is consistent with a formula for the anhydrous material of $Mg_4Al_2(OH)_{12}(Par)_{0.81}(NO_3)_{0.36}(OH)_{0.83}$ where Par is the anion of Parsol 1789. The x-ray diffraction pattern showed
 i) that the only crystalline material present was a layered double hydroxide.
 ii) there were major lines present at 14.9A and 11.4A which were not present in the starting material and which are characteristic of a Parsol 1789 exchanged material.

Example 15

Preparation of zinc Aluminium Hydroxy Nitrate
Zinc aluminium hydroxy nitrate was prepared by the method described in Example except that the magnesium oxide was entirely replaced by 94.5 g of zinc oxide.

The chemical composition of the material was determined by analysis. The results were as follows

| Mole ratio Zn/Al | = | 2.0 |
| % ZnO + $Al_2O_3$ | = | 61.5 |
| % $H_2O$ (from dehydroxylation) | = | 12.9 |
| % $NO_3$ | = | 17.8 |

This is consistent with an idealised formula for the anhydrous material of $Zn_4Al_2(OH)_{12}(NO_3)_2$ The x-ray diffraction pattern of the hydrated material showed
 i) the only crystalline material present was a layered double hydroxide analogous to hydrotalcite. Characteristic line spacings at 1.51A and 1.53A were present.
 ii) the presence of a major line at 8.8A, which has been shown to be characteristic of this interlayer nitrate containing material.

Example 16

Ion-exchange of 2-Phenylbenzimidazole-5-sulphonate into Zn/Al layered double hydroxide
19.65 g of 2-Phenylbenzimidazole-5-sulphonate was dissolved/suspended in 150 ml of water. 2.87 g of sodium hydroxide was dissolved in 50 ml of water, and then added to the suspension to give a clear solution. This solution was then added to 25 g of the nitrate form of layered double hydroxide made in Example 15 in a 250 ml polypropylene screwcap bottle. The bottle was capped, shaken for 2 minutes and then heated at 90° C. for 18 hours. The solid was filtered off, washed with warm water and then freeze dried. The product was finally equilibrated with water vapour by storing in a dessicator over a saturated sodium chloride solution.

The chemical composition of the material was determined by thermal end elemental analysis. The results were as follows

| % ZnO + $Al_2O_3$ | = | 37.27 |
| % C | = | 26.30 |

This is consistent with an idealised formula for the anhydrous material of $Zn_4Al_2(OH)_{12}(pbs)_{1.94}(NO_3)_{0.06}$ the x-ray diffraction pattern showed
 i) the only crystalline material present to be a layered double hydroxide.
 ii) there was a major line et 22A, which was not present in the starting material.

Example 17

Ion-exchange of Benzophenone-4 into Zinc Aluminium Hydroxy Nitrate
5.6 g of sodium hydroxide was dissolved at room temperature in 225 ml of deionized water. To this was added 21.5 g of Benzophenone-4. The mixture was stirred until the Benzophenone-4 completely dissolved. The resulting solution was then transferred to a bottle containing 25 g of the zinc aluminium hydroxy nitrate prepared as described in Example 15. This mixture was shaken and placed in an oven at 95° C. for 18 hours. The solid was filtered, washed with 1500 ml of 80° C. water, filtered again, and finally freeze dried. A free-flowing yellow powder was obtained.

The chemical composition of this material was determined by analysis. The results were as follows

| | | |
|---|---|---|
| % ZnO + Al$_2$O$_3$ | = | 49.0 |
| % C | = | 18.0 |

This is consistent for a formula for the anhydrous material of $$Zn_4AL_2(OH)_{12}(Benz)_{0.94}(NO_3)_{0.05}$$

where Benz is an anion derived from Benzophenone-4. In this case, the Benzophenone-4 seems to be located in the structure exclusively in the dianion form. This is supported by the x-ray diffraction data.

The x-ray diffraction data showed that:
i) the only crystalline material present was layered double hydroxide.
ii) there was a major line at 13.5Å which was not present in the starting material (the 13.5Å line corresponds to layers which contain predominantly the divalent species).

Such a divalent species is preferred when it is desired to obtain enhanced UV-A protection from the composition.

Example 18

Preparation of Calcium Aluminium Hydroxy Nitrate

Solution 1: 25 g of sodium hydroxide and 36.4 g of sodium nitrate were dissolved in 175 ml of water.

Solution 2: 68.1 g of calcium nitrate tetrahydrate and 46.8 g of aluminium nitrate nonahydrate were dissolved in 325 ml of water.

Solution 1 was placed in a 1 liter polypropylene bottle. Solution 2 was then slowly added to the bottle over about 1 hour. The contents of the bottle were stirred vigorously throughout the addition of solution 2. The bottle was capped and placed in a 90° C. oven for 7 days. The solid was filtered off, washed with water, freeze dried and finally equilibrated with water vapour as described in Example 1.

X-ray diffraction showed the product to contain a layered double hydroxide with a basal spacing of 8.5A together with a small amount of unidentified material.

Example 19

Ion-exchange of 2-Phenylbenzimidazole-5-sulphonate into Ca/Al layered Double Hydroxide 13.8 g of 2-Phenylbenzimidazole-5-sulphonate was dissolved/suspended in 150 ml of water. 2.0 g of sodium hydroxide was dissolved in 150 ml of water, and then added to the suspension to give a clear solution. This solution was then added to 15 g of the nitrate form layered double hydroxide formed in Example 18 in a 250 ml polypropylene screwcap bottle. The bottle was capped, shaken for 2 minutes and then heated at 90° C. for 18 hours. The solid was filtered off, washed with warm water and then freeze dried. The product was finally equilibrated with water vapour by storing in a dessicator over a saturated sodium chloride solution.

The x-ray diffraction pattern of the product showed no evidence of the 8.5A diffraction line which was characteristic of the starting material. Instead there was a major line at 22A, which was not present in the starting material.

The chemical composition of the material was determined by thermal and elemental analysis. The results were as follows

| | | |
|---|---|---|
| % CaO + Al$_2$O$_3$ | = | 43.12% |
| % C | = | 23.40% |

This is consistent with the material containing 41% by weight 2-Phenylbenzimidazole-5-sulphonate.

Example 20

Effect of Salt (Sodium Chloride) on Retention of the Anionic Sunscreen by the Hydrotalcite 1 g of material as prepared in Example 2 was dispersed in 50 ml of water containing 0.2 g of sodium chloride (more chloride ion than would be required for a stoichiometric replacement of the cinnamate ions). The suspension was stirred for 2 hours at room temperature and the solid was filtered off. The filtrate was then analysed by uv spectroscopy for the presence of cinnamate ion. The amount found was consistent with the removal of only 3% of the cinnamate from the layered double hydroxide.

Example 21

Preparation of Sunscreen Composition

An oil phase was prepared by mixing and heating to 75° C.:

| | |
|---|---|
| Mineral oil (Sirius M85) | 10.0% |
| Nafol 16/18 | 2.0% |
| Glycerol monostearate | 0.5% |
| Polyoxyethylene (20) cetylether | 0.5% |

Amounts ere percentages by weight of the final product. Nafol 16/18 is a mixture of palmityl alcohol and stearyl alcohol.

| | |
|---|---|
| water, demineralized | 74.7% |
| glycerol | 2.0% |
| xanthan gum | 0.3% |

This aqueous phase was prepared by adding the glycerol to the water end then mixing in the Rhodopol with a high sheer mixer. (Silverson mixer).

Both phases were then heated to 75° C. and mixed in the high sheer mixer, after which was added Layered double hydroxide 10%

The emulsion was then left to cool.

The layered double hydroxide was prepared in Example 6 above. However it would be possible to use layered double hydroxides as prepared in any of examples 2 to 10, 16, 17 or 19 above.

It would also be possible to use a mixture of double hydroxides with different interlayer anions, e.g. products of examples 4 and 7 in equal amounts or products of examples 7 and 8 in equal amounts.

If desired a colouring pigment may be added in small amount to the aqueous phase, with corresponding reduction in the amount of water.

Example 22 (comparative) and Example 23

Preparation and Characterization of Sunscreen compositions containing Benzophenone-4, both free and incorporated into Zinc Aluminium Hydroxy Nitrate Sunscreen products were prepared with the compositions given in Table I below. The procedure for preparing these sunscreen products was as follows: the butylene glycol, dimethicone copolyol, EDTA, water, glycerin, Germaben, and the UV absorber were mixed using a high shear homogenizer at room temperature for 10 minutes to give mixture A. For Example 22 the sunscreen active was Benzophenone-4 itself. For Example 23 the sunscreen active was zinc aluminium hydroxy nitrate with Benzophenone-4 exchanged into it as in Example 17. In a separate container, the octyldodecyl neopentanoate, propylene glycol isoceteth-3 acetate, cetyldimethicone and octyl methoxycinnamate were dissolved together and added to the above described mixture A. The pH of this mixture was then adjusted to a value of 7.6 to 7.9 using either triethanolamine or aqueous hydrochloric acid as required. Emulsions were obtained which were then used for in vitro SPF testing as described below.

In order to evaluate the efficacy of the formulations for protection against UV radiation in sunscreens, a well established in vitro Sun Protection Factor (SPF) method was used. It is described by Diffey et al. (Diffet, BL, and Robson, J, "A New Substrate to Measure Sunscreen Protection Factors throughout the Ultra-violet Spectrum", J. Soc. Cosmet. Chem., 40, 127–133, (1989)). This method consists in essence of applying (by rubbing) a standard amount of a sunscreen composition (2 mg/cm$^2$) onto a piece of special tape (Transpore, ex. 3M Company) which has a surface roughness approximating that of human skin. The diffuse transmittance spectrum of the film of sunscreen emulsion is then measured over the range of 290 to 400 nm in a specially adapted spectrophotometer. The ordinary (erythemal) SPF is calculated from the spectral data in the manner described in the above reference by Diffey et al. UV-A protection factors are calculated as the reciprocal of the average transmittance of the sunscreen film over the wavelength range 320 to 400 nm.

The results of these measurements on the sunscreen compositions of Example 22 and Example 23 are (an average of three to five replicate measurement were made on each composition) given in Table II below.

It is seen that the sunscreen product of Example 23 containing Benzophenone-4 ion-exchanged into the layered double hydroxide provides protection from UV radiation across a broad range of wavelengths substantially better than the sunscreen product in comparative Example 22 where the Benzophenone-4 is not ion-exchanged into a layered double hydroxide.

TABLE I

SUNSCREEN COMPOSITIONS OF EXAMPLES 22 AND 23

| Component | Example 22 | Example 23 |
|---|---|---|
| Octyl Methoxycinnamate[1] | 7.0% | 7.0% |
| Benzophenone-4 | 5.85% | none |
| Benzophenone-4 (30% exchanged into zinc aluminum hydroxy nitrate as in Example 17) | none | to give 5.85% Benzophenone-4 |
| Octyldodecyl Neopentanoate[2] | 5.5% | 5.5% |
| Propylene Glycol Isoceteth-3 Acetate[3] | 6.5% | 6.5% |
| Cetyl Dimethicone[4] | 1.0% | 1.0% |
| Dimethicone Copolyol[5] | 0.6% | 0.6% |
| Butylene Glycol[6] | 6.0% | 6.0% |
| Glycerin[7] | 3.0% | 3.0% |
| Preservatives (EDTA, Germaben[8]) | 1.1% | 1.1% |
| Water | to 100% | to 100% |
| Triethanolamine, Aqueous | to adjust pH to 7.6 | to adjust pH to 7.9 |
| Hydrochloric Acid | | |

[1] Obtained from Van Dyk Co.
[2] Obtained from Bernel Chemical Company Inc.
[3] Obtained from Bernel Chemical Company Inc; chemical name is propylene glycol polyethylene glycol (3)isocetyl ether acetate.
[4] a silicone compound obtained from Dow Corning Corp.
[5] a silicone copolymer obtained from Dow Corning Corp.
[6] Obtained from Hoechst Celanese Corp.
[7] Obtained from Baker Corp.
[8] A preservative containing diazolidinyl urea, propylene glycol, methyl paraben, propylparaben. Obtained from Sutton Laboratories

TABLE II

In vitro SPF Measurements on Sunscreen Compositions

| Example | Calculated Erythemal in vitro SPF | Average UVA Protection Factor |
|---|---|---|
| Example 22 (no layered double hydroxide) | 16.2 | 3.0 |
| Example 23 (with layered double hydroxide) | 43.9 | 6.0 |

| Example | Calculated Erythemal in vitro SPF | Average UVA Protection Factor |
|---|---|---|
| Example 24 (no layered double hydroxide) | 4.6 | 2.2 |
| Example 25 (with layered double hydroxide) | 11.2 | 6.0 |

TABLE III

Sunscreen Compositions of Examples 24 and 25

| Component | Example 24 | Example 25 |
|---|---|---|
| Benzophenone-4 | 5.0% | 5.0% |
| Dow Drilling Fluid Additive XUS 50165.05L | None | 68.0% |
| Aqueous 50% Sodium Hydroxide | 1.9% | 1.9% |
| Octyl Methoxycinnamate[1] | 7.5% | 7.5% |
| Steareth-2[2] | 1.0% | 1.0% |
| Steareth-21[3] | 4.0% | 4.0% |
| Amorphous Precipiated Silica[4] | 3.5% | 3.5% |
| Glycerin[5] | 2.0% | 2.0% |
| Preservative (Glydant Plus)[6] | 0.2% | 0.2% |
| Aqueous Hydrochloric Acid | to adjust pH to 7.5 | to adjust pH to 7.5 |

TABLE III-continued

Sunscreen Compositions of Examples 24 and 25

| Component | Example 24 | Example 25 |
|---|---|---|
| Water | to 100% | to 100% |

[1] From Haarmann and Reimer Co.
[2] Tradename Brij 72, from ICI Americas, Inc., the chemical name of this material is polyoxyethylene (2) stearyl ether.
[3] Tradename Brij 721, from ICI Americas, Inc., the chemical name of this material is polyoxyethylene (21) stearyl ether.
[4] Tradename Sident 22S, from Degussa Corporation, this material is a synthetic amorphous silicon dioxide hydrate.
[5] From Baker Corporation.
[6] Obtained from Lonza Corporation, this preservative is a mixture of DMDM Hydrantoin (1,3-dimethylol-5,5-dimethyl hydrantoin) and Iodopropynyl Butylcarbamate (butyl-3-iodo-2-propynylcarbamate).--

We claim:

1. A sunscreen composition for application to human skin comprising an effective amount of:
   (i) cosmetically acceptable vehicle; and incorporating
   (ii) from 0.05% to 50% by weight of the composition of a layered double hydroxide of the formula $$[M_m N_n (OH)_{2(m+n)}]^{p+} X^{x-}_{y/x} \cdot zH_2O \qquad (I)$$

wherein N is one or a mixture of trivalent metal ions selected from the group consisting of aluminum, chromium, iron, nickel, manganese, and scandium M is a divalent metal ion selected from the group consisting of magnesium, zinc, calcium, cobalt, nickel, copper, manganese and iron, or is lithium, if M is divalent y=n and if M is lithium y=(n-m), and X denotes interlayer anions, from 5 to 100 mole % of which display ultraviolet absorption with a molar extinction coefficient of at least $2 \times 10^3$ over at least a portion of the wavelength range from 290 to 400 nanometers.

wherein said layered double hydroxide is dispersed in said vehicle.

2. The composition of claim 1 in which the trivalent metal is aluminium.

3. The composition of claim 1 in which the metal M is selected from the group consisting of magnesium, zinc or calcium.

4. The composition of claim 1 in which the metal M is lithium.

5. The composition of claim 1 wherein at least 5 mole % of the interlayer anions X are selected from the group consisting of the anions of:
   para amino benzimidazole-5-sulphonate
   3-imidazol-4-ylacrylate
   salicylate
   p-methoxy cinnamate
   2 ethyl hexyl-2-cyano-3,3 diphenyl acrylate
   3,3,5 trimethylcyclohexyl-2-acetamido benzoate
   cinnamate
   p-aminobenzoate
   3,4-dimethoxy phenyl glyoxylate
   α-(2-oxoborn-3-ylidene)-p-xylene-2-sulphonate
   α-(2-oxoborn-3-ylidene)toluene-4-sulphonate
   α-cyano-4-methoxy cinnamate
   2-phenyl benzimidazole-5-sulphonate and mixtures thereof.

6. The composition of claim 1 wherein at least 5 mole % of the interlayer anions X are anions of phenolic compounds which display ultraviolet absorption over at least a portion of the wavelength range from 200 to 400 nm.

7. The composition of claim 6 wherein of the interlayer anions X are anions of compounds comprising a hydroxylated benzophenone moiety.

8. The composition of claim 6 wherein at least 5 mole % of the interlayer anions X are anions of a compound selected from the group consisting of:
   Benzophenone-1
   Benzophenone-2
   Benzophenone-3
   Benzophenone-4
   Benzophenone-5
   Benzophenone-6
   Benzophenone-7
   Benzophenone-8
   Benzophenone-9
   Benzophenone-10
   Benzophenone-12
   and mixtures thereof.

9. The composition of claim 8 wherein a majority of the interlayer anions X are selected from the group defined in claim 12.

10. The composition of claim 1 wherein a majority of the interlayer anions X are anions of Butyl Methoxydibenzoylmethane.

11. The composition of claim 1 wherein a majority of the interlayer anions X are anions of 1-(4-methoxy-5-benzofuranyl)-3-phenyl-1,3-propanedione.

12. The composition of claim 7 wherein a majority of the interlayer anions X are anions of a compound selected from the group consisting of homomenthyl salicylate and 2-ethylhexyl salicylate.

13. The composition of claim 8 wherein a majority of the interlayer anions X are anions of Benzophenone-4.

14. A sunscreen method for application to human skin comprising an effective amount of:
   (i) a cosmetically acceptable vehicle; and
   (ii) from 0.05% to 50% by weight of the composition of a layered double hydroxide of the formula $$[M_m N_n (OH)_{2(m+n)}]^{p+} X^{x-}_{y/x} \cdot zH_2O \qquad (I)$$

wherein N is one or a mixture of trivalent metal ions selected from the group consisting of aluminum, chromium, iron, nickel, manganese, and scandium, M is a divalent metal ion selected from the group consisting of magnesium, zinc, calcium, cobalt, nickel, copper, manganese and iron, or is lithium, if M is divalent y=n and if M is lithium y=(n-m), and X denotes interlayer anions, from 5 to 100 mole % of which display ultraviolet absorption with a molar extinction coefficient of at least $2 \times 10^3$ over at least a portion of the wavelength range from 290 to 400 nanometers, wherein said layered double hydroxide is dispersed in said vehicle.

15. The method of claim 14 in which the trivalent metal is aluminium.

16. The method of claim 14 in which the metal M is selected from the group consisting of magnesium, zinc or calcium.

17. The method of claim 14 in which the metal M is lithium.

18. The method of claim 14 wherein at least 5 mole % of the interlayer anions X are selected from the group consisting of the anions of:

para amino benzimidazole-5-sulphonate
3-imidazol-4-ylacrylate
salicylate
p-methoxy cinnamate
2 ethyl hexyl-2-cyano-3,3 diphenyl acrylate
3,3,5 trimethylcyclohexyl-2-acetamido benzoate
cinnamate
p-aminobenzoate
3,4-dimethoxy phenyl glyoxylate
α-(2-oxoborn-3-ylidene)-p-xylene-2-sulphonate
α-(2-oxoborn-3-ylidene)toluene-4-sulphonate
α-cyano-4-methoxy cinnamate
2-phenyl benzimidazole-5-sulphonate; and
mixtures thereof.

* * * * *